United States Patent [19]

Miyazawa et al.

[11] Patent Number: 5,084,392
[45] Date of Patent: Jan. 28, 1992

[54] PROCESS FOR PRODUCING OPTICALLY ACTIVE HYDROXY LACTONES

[75] Inventors: Kazutoshi Miyazawa; Naoyuki Yoshida, both of Ichihara, Japan

[73] Assignee: Chisso Corporation, Osaka, Japan

[21] Appl. No.: 626,290

[22] Filed: Dec. 12, 1990

[30] Foreign Application Priority Data

Feb. 2, 1990 [JP] Japan .................. 2-22054

[51] Int. Cl.$^5$ ............................. C12P 41/00
[52] U.S. Cl. ................... 435/280; 435/125; 435/126; 435/135; 549/292; 549/313
[58] Field of Search ............... 549/292, 313; 435/125, 435/126, 288

[56] References Cited

U.S. PATENT DOCUMENTS

| 4,489,208 | 12/1984 | Olivieri et al. | 435/280 |
| 4,916,074 | 4/1990 | Yoshida et al. | 435/134 |
| 4,962,031 | 10/1990 | Yoshida et al. | 435/128 |
| 4,971,909 | 11/1990 | Kaneoya et al. | 435/122 |

FOREIGN PATENT DOCUMENTS

| 0337920 | 10/1989 | European Pat. Off. | 435/125 |
| 0371568 | 6/1990 | European Pat. Off. | 435/126 |
| 1010996 | 1/1989 | Japan | 435/126 |

OTHER PUBLICATIONS

Mori et al., Tetrahedron, 35, 933 (1979).
Hayashi et al., J. Am. Chem. Soc., 95, 8749 (1973).
Luk et al., Synthesis, 3, 226 (1988).
Seebach, Synthesis, 1, 37 (1986).
Meyers, Tetrahedron Letters, 29, 5617 (1988).
Bevinakatti, J. Org. Chem., 54, 2453 (1989).

Primary Examiner—C. Warren Ivy
Assistant Examiner—Amelia A. Owens
Attorney, Agent, or Firm—Wenderoth, Lind & Ponack

[57] ABSTRACT

The invention provides a method for producing an optically active hydroxy lactone which comprises reacting under substantially anhydrous conditions and in the presence of an enzyme an ester and a racemic compound represented by the general formula (I):

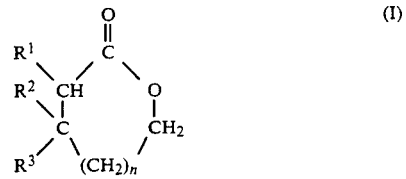

wherein n is 0 or 1, any one of $R^1$ and $R^2$ is a hydroxy group, and $R^2=R^3=H$ or $R^2=R^3=CH_3$ when $R^1$ is the hydroxy group, and $R^1=R^3=H$ when $R^2$ is the hydroxy group, to effect a transesterification reaction, and resolving to an optically active alcohol which has R- or S-configuration and the ester of the symmetric alcohol.

4 Claims, No Drawings

PROCESS FOR PRODUCING OPTICALLY ACTIVE HYDROXY LACTONES

BACKGROUND OF THE INVENTION

The present invention relates to a process for producing optically active compounds which are used as starting materials for optically active and physiologically active compounds, functional materials, etc., especially optically active hydroxy lactones.

Optically active compounds are useful as starting materials for physiologically active compounds such as pharmaceuticals, agricultural chemicals and so on, and functional materials, and as intermediates. However, since the compounds have optical isomers, one of the enantiomers is essentially used in practice. When the racemic compounds or compounds having a low optical purity are used, apparently no compounds having adequate physiological activity or functionality are obtained.

Optically active compounds obtained by the process of the present invention, namely hydroxy lactones, are very useful compounds. Nevertheless, an effective process of producing the compounds is unknown.

For instance, although a process for preparing derivatives from malic acid or malate obtained in nature is well-known, it is necessary to reduce either of two carboxyl groups or either of two esters. However, an effective process is unknown and the above process is not useful industrially. For obtaining an enantiomer, malic acid as the starting material which is not a natural type should be used. Since the compound is more expensive than that of a natural type, it is disadvantageous industrially for use as the starting material. (K. Mori et al., Tetrahedron, 35, 933(1979), H. Hayashi et al., J. Am. Chem. Soc., 95, 8749(1973), E. J. Corey et al., J. Am. Chem. Soc., 100, 1942(1978), S. J. Shiuey et al , J. Org. Chem., 53, 1040(1988)).

In addition, a process in which L-ascorbic acid is used as a starting material is known. However, the process is troublesome and disadvantageous (K. C. Luk et al., Synthesis, 3, 226(1988)).

Lately, a process for obtaining R-3-hydroxybutyrolactone is found by using baker's yeast. In the process, the effect of an asymmetrical reduction step in which the baker's yeast is used is not good. Namely, for example, one kg of baker's yeast, one kg of sucrose and 8 liters of water are used for treating only 35 g of substrate. The treatment is disadvantageous industrially. In the process, it is impossible to obtain an S-compound. For obtaining the S-compound, the other process should be studied. (D. Seebach, Synthesis, 1, 37(1986)).

Moreover, a method in which a prochiral ketone is asymmetrically reduced with optically active 4-methyl-1,4-dihydro pyridine to obtain S-pantolactone is known. Since the asymmetrical yield is low (about 72% ee), the method is rather impractical. (A. I. Meyers, Tetrahedron Letters, 29, 5617(1988)).

Further, a method for obtaining R- or S-pantolactone by an asymmetric alcoholysis in the presence of lipase has been reported. According to the method, it is possible to obtain both enantiomers. Although, it seems as if the method is excellent, the optical purity of the R-compound is 70% ee and that of S-compound is 36% ee. As a result, the method is impractical. (H. S. Bevinakatti, J. Org. Chem., 54, 2453(1989)).

As described above, the conventional methods have many problems. Firstly, starting materials obtained from natural products via many steps are expensive. Secondarily, since substrate concentration in a process of asymmetrical reduction is very low, the method is unsuitable for mass production. Thirdly, since only either enantiomer is obtainable, the other enantiomer should be obtained by a different method. Fourthly, it is impossible to obtain a compound having high purity.

SUMMARY OF THE INVENTION

The object of the present invention is to solve the above disadvantages of the conventional methods and to provide a new and useful method for producing optically active hydroxy lactones.

The present invention provides a method for producing an optically active hydroxy lactone which comprises reacting under substantially anhydrous conditions and in the presence of an enzyme an ester and a racemic compound represented by the general formula (I):

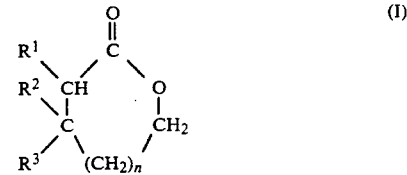

wherein n is 0 or 1, either one of $R^1$ and $R^2$ is a hydroxy group, and $R^2=R^3=H$ or $R^2=R^3=CH_3$ when $R^1$ is the hydroxy group, and $R^1=R^3=H$ when $R^2$ is the hydroxy group, to effect a transesterification reaction, and resolving to an optically active alcohol which has R- or S-configuration and the ester of the symmetric alcohol.

DETAILED DESCRIPTION OF THE INVENTION

In the method of the present invention, the reaction is conducted under anhydrous conditions. This method does not require the use of a small amount of water or a lower alcohol instead of the water, and a side reaction does not occur such as hydrolysis of obtained ester and esters of starting compounds, and formation of undesirable esters scarcely occurs, so that the enzyme is stably kept in organic solvent and easily separated after the reaction and reused. Furthermore, as the enzyme is directly used and reacted in organic solvent, the method can be kept free from contamination by unwanted microorganisms. Accordingly, there is no necessity for special equipment, antiseptics, sterilization treatment, etc. It is possible to conduct the reaction in an open system. Further, the reaction may be conducted in the same or less quantity of solvent in comparison with common organic synthetic reactions in high substrate concentration.

It is also enough to use esters which are commercially available without any difficulty for transesterification. Ethyl acetate, ethyl propionate, ethyl butyrate, triacetin, tributyrin, tricaproin, etc., can be used. Especially, vinyl esters are preferable. Vinyl acetate, vinyl caproate, vinyl laurate, etc. can be exemplified as such vinyl esters.

As the enzyme usable in the present invention, hydrolase can be used, especially a lipase, lipoprotein lipase, esterase, etc., are preferable. However, the enzyme having the ability to catalyze a transesterification reaction preferentially between the R- or S-compound and the ester when the enzyme is used with the racemic compound can be used regardless of its class. For example, the following table shows commercially available enzymes that can be used in the present reaction.

TABLE

| Trade name | Origin | Seller or Maker |
| --- | --- | --- |
| Lipase AP | Aspergillus niger | Amano Pharmaceutical Co., Ltd |
| Lipase M | Mucor javanicus | Amano Pharmaceutical Co., Ltd |
| Lipase P | Pseudomonas fluorescens | Amano Pharmaceutical Co., Ltd |
| Lipase PS | Pseudomonas fluorescens | Amano Pharmaceutical Co., Ltd |
| Lipase CES | Pseudomonas sp | Amano Pharmaceutical Co., Ltd |
| Lipase CE | Humicola lanuginosa | Amano Pharmaceutical Co., Ltd |
| Lipase AP | Rhizopus javanicus | Amano Pharmaceutical Co., Ltd |
| Lipase II | Porcine pancreas | Sigma Chemical Co., Ltd |
| Lipase VIII | Geotrichum candidum | Sigma Chemical Co., Ltd |
| Lipase X | Rhizopus delamar | Sigma Chemical Co., Ltd |
| Lipase | Chromobacterium viscosum | Toyo Jozo Co., Ltd |
| Palatase A | Aspergillus niger | Novo Industi A/S |
| Lipase | Rhizopus niveus | Nagase Biochemicals, Co. Ltd |
| Lipase B | Pseudomonas flaji | Sapporo Beer Co., Ltd |

In addition to these enzymes, microorganisms which produce the enzymes having the above ability can be used regardless of their species and genus. As such microorganisms, the genera Arthrobacter, Acromobacter, Alcaligenes, Aspergillus, Chromobacterium, Candida, Mucor, Pseudomonas, Rhizopus, etc., can be exemplified. The enzymes produced from these microorganisms can be used also.

The following description illustrates the process of the present invention more specifically.

In the present invention, the racemic compounds represented by the formula (I) of starting materials can be easily prepared by conventional organic chemical methods. For example, the following steps are advantageously used.

When $R^1$ is a hydroxy group in the formula (I),

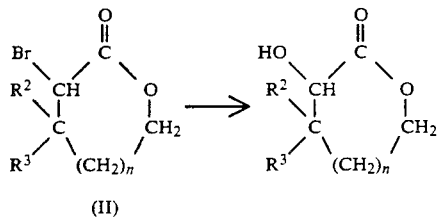

(II)

wherein $R^2$ and $R^3$ are hydrogen or a methyl group, respectively.

Namely, the compound can be easily obtained by the reaction of the above bromide (II) which is commercially available. (J. Prakt. Chem. 17, 91(1985)).

When $R^2$ is a hydroxy group in the formula (I),

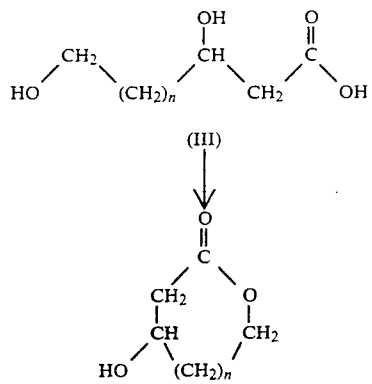

(III)

wherein $R^1 = R^3 = H$ in the formula (I).

In the above formula, R is alkyl or hydrogen and n is 0 or 1.

Namely, the diol compound (III) which can be easily obtained by using a common organic chemical method, is reacted under acidic conditions to obtain the lactone.

In the present invention, the reaction is conducted by mixing a racemic compound and an ester and by efficiently contacting the mixture with an enzyme.

The racemic compound and the ester can be used without any particular treatment. When the racemic compound which is a substrate is soluble in the ester, the reaction can be conducted without adding a solvent. When the racemic compound is slightly soluble in the ester, an organic solvent such as heptane or toluene may be added.

The reaction temperature is suitably 0° to 100° C., and especially preferably 15° to 45° C. The most suitable temperature and the reaction time depend on the kind of the enzyme.

The reaction time is 5 to 240 hours. The time can be shortened by elevating the reaction temperature or using an enzyme having high activity or lowering the substrate concentration.

The racemic compound which is a substrate and the ester are suitably mixed in the ratio 1:0.5 to 1:2 by mole, and preferably 1:1.1 to 1:2.0 by mole.

After the transesterification reaction, the enzyme can be removed by conventional filter operation and used again, as it is. The reaction can be repeated by fixing the enzyme to absorb on hydrophobic resin or the like. The reactant which is the filtrate can be separated into an optically active alcohol and an optically active ester which is an antipode of the alcohol, respectively, for example by distillation or column chromatography. The ester obtained is hydrolyzed to derive an optically active alcohol which is an antipode of the above alcohol.

The optically active alcohol, which has R- or S-configuration, is represented by the formula:

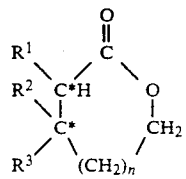

wherein n is 0 or 1, any one of $R^1$ and $R^2$ is a hydroxy group, and $R^2 = R^3 = H$ or $R^2 = R^3 = CH_3$ when $R^1$ is the hydroxy group, and $R^1=R^3=H$ when $R^2$ is the hydroxy group, and * shows that the carbon is an asymmetric atom when the carbon binds to the hydroxy group.

The optically active compounds obtained by the above operation show small difference in optical purities depending on the structures. The optical purities can be raised by re-transesterification reaction.

The merits of this invention are as follows.
(1) Unnecessary hydrolysis of esters scarcely occurs because the transesterification reaction is substantially conducted under the conditions of no water.
(2) The enzyme can be easily recovered and reused.
(3) No special equipment and materials are used because the reaction can be performed under the conditions of relatively lower temperatures and an open system.
(4) Optically active substances having high purity are obtained by a one-step reaction.
(5) In spite of the biochemical reaction, the substrate concentration can be increased and big reaction vessels are unnecessary, because a buffer solution and the like are not required in the reaction.
(6) The optically active compounds prepared by the method of the present invention are important as starting materials of many kinds of useful compounds.

The embodiments are shown in the following.

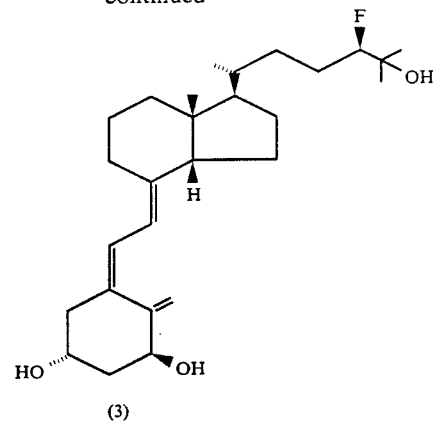
(3)

S-α-hydroxy-γ-butyrolactone (1) which can be prepared by the method of the present invention is easily changeable to R-α-fluoro-γ-butyrolactone (2). The latter compound is useful for a starting material of 1α, 25-dihydroxy-24(R)-fluorocholecalsiferol (3) (S. J. Shiuey et al., J. Org. Chem., 53, 1040(1988)).

R-α-hydroxy-γ-butyrolactone which is the antipode of (1) is useful for a starting material of 2,3-epoxy-squalene (M. A. Abdallah et al., J. Chem. Soc., Perkin Trans., 1, 888(1975)).

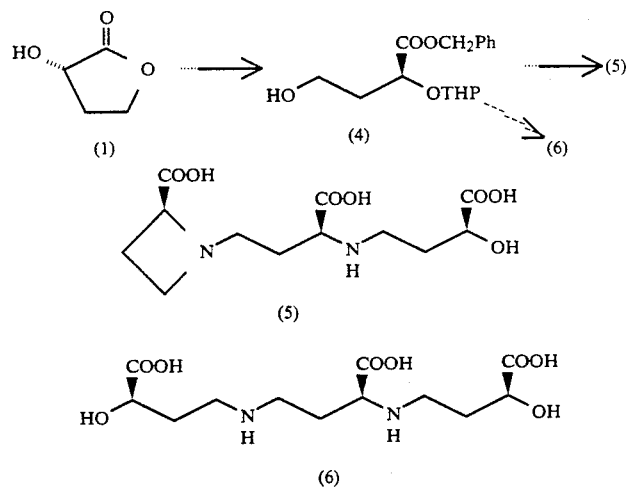

Further, after a protective substrate is introduced into S-α-hydroxy-γ-butyrolactone (1), ring opening reaction of the compound provides the compound (4) which is a starting mateial for producing mugineic acids (5) and (6) (Japanese Patent Unexamined Publication Nos. 57-112384 and 57-112385).

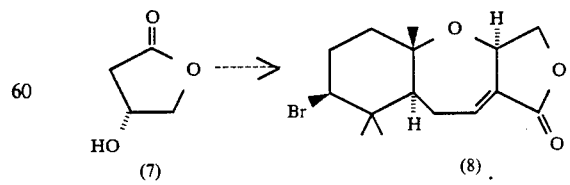

R-β-hydroxy-γ-butyrolactone (7) is useful for a starting material of the production of (−)-aplysistatine (8) which is an anticancer agent (H. M. Shieh, Tetrahedron Letters, 23, 4643(1981)).

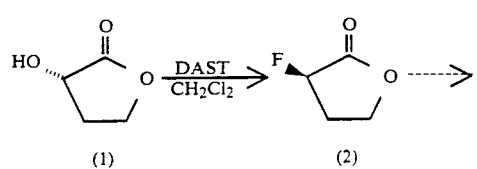

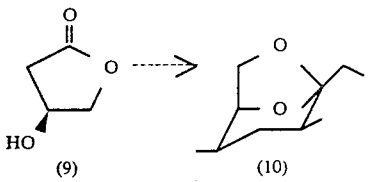

S-β-hydroxy-γ-butyrolactone (9) which can be produced by the method of the present invention is a starting material for synthesizing (−)-α-multistriatin (10) which is an insect pheromone (M. Larcheveque et al., Tetrahedron, 43, 2303(1987)).

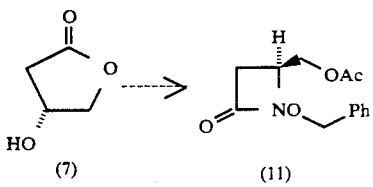

Moreover, the compound (7) from which S-N-benzyloxy-4-acetoxymethyl-2-azetidinone (11) can be derived is usable as an intermediate for producing carbapenem type antibiotics (H. Yamada et al., Heterocycles, 26, 2841(1987)).

Further, R-β-hydroxy-γ-butyrolactone (7) or S-β-hydroxy-γ-butyrolactone (9) can be converted into R- or S-1,2,4-butanetriol or a derivative thereof. These compounds can be used for synthesizing (+)-ipsdienol (K. Mori et al., Tetrahedron, 35, 933(1979)), mevinolin and compactin (Y. Guindon et al., Tetrahedron Letters, 26, 1185(1985)), S-3-piperidinol (R. K. Olsen et al., J. Org. Chem., 50, 896(1985)), tulipalin B (C. Papageorigiou et al., J. Org. Chem., 50, 1144(1985), aglycone (S. Hanessian et al., J. Org. Chem., 48, 4427(1983)), dihydroxypentyluracil (H. Hayashi et al., J. Am. Chem. Soc., 95, 8749(1973)), etc.

DESCRIPTION OF PREFERRED EMBODIMENTS

The present invention is illustrated by the following examples. In the examples, the optical purities of the optically active compounds are determined by comparison of specific rotation with compounds having known optical purities in literatures and by HPLC analysis using an optically active resolution column which is commercially available.

EXAMPLE 1

Optical resolution of α-hydroxy-γ-butyrolactone (in formula (I), n=0, $R^1$=OH and $R^2$=$R^3$=H).

(i) A mixture of 2.0 g of racemic α-hydroxy-γ-butyrolactone, 1.01 g of vinyl acetate and 0.2 g of lipase PS (manufactured by Amano Pharmaceutical Co., Ltd.) was reacted with stirring at 20° C. for 75 hours. After the reaction was stopped, the enzyme was removed by suction filtration, and the residue was purified with a chromatograph over silica gel to obtain 1.09 g of S-α-hydroxy-γ-butyrolactone, $[\alpha]_D^{26}$−37.1°(C 1.18, $CHCl_3$) and 1.3 g of R-α-acetoxy-γ-butyrolactone. 5 ml of ethanol and 3 drops of concentrated sulfuric acid were added to 1.3 g of R-α-acetoxy-γ-butyrolactone. The mixture was reacted with stirring at 40° C. for 5 hours and deacetylated. 0.84 g of R-α-hydroxy-γ-butyrolactone (yield: 84%) was obtained. 93% ee.

$[\alpha]_D^{30}$+61.2°(C 1.07, $CHCl_3$) $^1$H-NMR δ2.1–2.8(m, 2H, $CH_2$), δ3.15(brs, 1H, OH), 4.1–4.7 (m, 3H, $CH_2O$, CHO)

(ii) 0.5 g of vinyl acetate and 0.1 g of lipase PS were added to 1.09 g of S-α-hydroxy-γ-butyrolactone obtained in (i). The mixture was reacted with stirring at 20° C. for 50 hours. After the reaction was stopped, the enzyme was removed by suction filtration, and the residue was purified with a chromatograph over silica gel to obtain 0.75 g of S-α-hydroxy-γ-butyrolactone (yield: 75%). 97.1% ee.

$[\alpha]_D^{26}$−63.3°(C 1.18, $CHCl_3$).

(Literature value: $[\alpha]_D^{25}$−65.2°(C 1.15, $CHCl_3$), S. J. Shiuey et al., J. Org. Chem., 53, 1040(1988)).

EXAMPLE 2

Optical resolution of α-hydroxy-β-dimethyl-γ-butyrolactone (pantolactone)(in formula (I), n=0, $R^1$=OH and $R^2$=$R^3$=H).

A mixture of 2.0 g of racemic α-hydroxy-β-dimethyl-γ-butyrolactone (pantolactone), 0.80 g of vinyl acetate, 1.0 g of lipase PS (manufactured by Amano pharmaceutical Co., Ltd.) and 6 ml of toluene was reacted with stirring at 20° C. for 150 hours. After the reaction was stopped, the enzyme was removed by suction filtration, and the residue was purified with a chromatograph over silica gel to obtain 1.1 g of S-α-acetoxy-β-dimethyl-γ-butyrolactone [(yield: 85%). 96.4% ee. $[\alpha]_D^{27}$+13.5°(C 1.26, EtOH). (Literature value: $[\alpha]_D^{25}$+14.0°(EtOH), S. Nabeta et al., Ger. Offen. 1948368 (1970)] and 0.71 g of R-α-hydroxy-β-dimethyl-γ-butyrolactone (yield: 71%). 80.1% ee.

$[\alpha]_D^{28}$−40.6°(C 1.05, $H_2O$).

(Literature value: $[\alpha]_D^{25}$−50.7°(C 2.05, $H_2O$), I. Ojima et al., Org. Synthesis, 63, 18(1984)).

EXAMPLE 3

Optical resolution of β-hydroxy-γ-butyrolactone (in formula (I), n=0, $R^2$=OH and $R^1$=$R^3$=H).

(i) A mixture of 1.0 g of racemic β-hydroxy-γ-butyrolactone, 0.5 g of vinyl acetate and 0.1 g of lipase PS (manufactured by Amano Pharmaceutical Co., Ltd.) was reacted with stirring at 25° C. for 48 hours. After the reaction was stopped, the enzyme was removed by suction filtration, and the residue was purified with a chromatograph over silica gel to obtain 0.32 g of S-β-hydroxy-γ-butyrolactone [$\alpha$ $_D^{28}$−19.7°(C 1.15, EtOH) and 0.35 g of R-β-acetoxy-γ-butyrolactone. To the S-compound, 5 ml of THF and 1 ml of an aqueous solution of 18N-$H_2SO_4$ were added. The mixture was reacted with stirring for 24 hours to obtain 0.25 g of deacetylated R-β-hydroxy-γ-butyrolactone. Yeild: 50%. 48.1% ee.

$^1$H-NMR($CDCl_3$/TMS)

δ62.52(dm, 1H, J=20Hz), 2.74(dd, 1H, J=20.7Hz), 3.02(d, 1H, J=4Hz), 4.30(dm, 1H, J=12Hz), 4.42(dm, 1H, J=12.5Hz), 4.67(m, 1H)

(ii) 0.16 g of vinyl acetate and 0.1 g of lipase PS were added to 0.32 g of S-β-hydroxy-γ-butyrolactone obtained in (i). The mixture was reacted with stirring at 25° C. for 48 hours. After the reaction was stopped, the enzyme was removed by suction filtration, and the residue was purified with a chromatograph over silica gel to obtain 0.20 g of S-β-hydroxy-γ-butyrolactone (yield: 40%). 85% ee.

$[\alpha]_D^{28}+65.7°$(C 0.90, EtOH). (Literature value: R-β-hydroxy-γ-butyrolactone $[\alpha]_D^{23}+77.3°$(C 2.0, EtOH), K. Mori et al., Tetrahedron, 35, 933(1979)).

We claim:

1. A process for producing an optically active hydroxy lactone, which comprises reacting under substantially anhydrous conditions and in the presence of an enzyme having the ability to catalyze a transesterification reaction, an ester which can be transesterified and a racemic compound represented by the general formula (I):

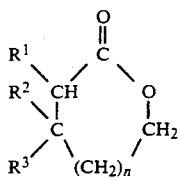

(I)

wherein n is 0 or 1, either one of $R^1$ and $R^2$ is a hydroxy group, and $R^2=R^3=H$ or $R^2=R^3=CH_3$ when $R^1$ is the hydroxy group, and $R^1=R^3=H$ when $R^2$ is the hydroxy group, to effect a transesterification reaction, and resolving to (1) an optically active alcohol which has R- or S-configuration represented by the formula:

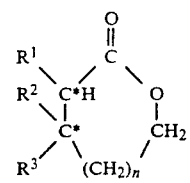

wherein n is 0 or 1, either one of $R^1$ and $R^2$ is a hydroxy group, and $R^2=R^3=H$ or $R^2=R^3=CH_3$ when $R^1$ is the hydroxy group, and $R^1=R^3=H$ when $R^2$ is the hydroxy group, and * shows that the carbon is an asymmetric atom when the carbon binds to the hydroxy group, and (2) the ester of the enantiomeric alcohol.

2. The process as claimed in claim 1, wherein the enzyme is lipase.

3. The process as claimed in claim 1, wherein the ester is a vinyl ester.

4. The process as claimed in claim 3, wherein the vinyl ester is vinyl acetate.

* * * * *